(12) United States Patent
Hirano et al.

(10) Patent No.: US 10,206,562 B2
(45) Date of Patent: Feb. 19, 2019

(54) METHOD FOR WASHING TREATMENT TOOL STAND

(71) Applicant: FUJIFILM Corporation, Tokyo (JP)

(72) Inventors: Souta Hirano, Kanagawa (JP); Tomohiro Ohki, Kanagawa (JP); Kazuya Takeuchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/893,706

(22) Filed: Feb. 12, 2018

(65) Prior Publication Data

US 2018/0160889 A1 Jun. 14, 2018

Related U.S. Application Data

(63) Continuation of application No. PCT/JP2016/070146, filed on Jul. 7, 2016.

(30) Foreign Application Priority Data

Aug. 17, 2015 (JP) .................................. 2015-160472

(51) Int. Cl.
*A61B 1/12* (2006.01)
*A46B 9/02* (2006.01)
(Continued)

(52) U.S. Cl.
CPC .............. *A61B 1/122* (2013.01); *A46B 9/028* (2013.01); *A46B 9/04* (2013.01); *A61B 1/00098* (2013.01);
(Continued)

(58) Field of Classification Search
CPC .................................................... A61B 1/122
(Continued)

(56) References Cited

U.S. PATENT DOCUMENTS 5,674,181 A 10/1997 Iida
2002/0017515 A1 2/2002 Obata et al.
(Continued)

FOREIGN PATENT DOCUMENTS

JP H07100098 4/1995
JP H08182648 7/1996
(Continued)

OTHER PUBLICATIONS

"International Search Report (Form PCT/ISA/210) of PCT/JP2016/070146," dated Sep. 27, 2016, with English translation thereof, pp. 1-5.

(Continued)

*Primary Examiner* — Roberts P Culbert
(74) *Attorney, Agent, or Firm* — JCIPRNET

(57) ABSTRACT

A method for washing a treatment tool stand of an endoscope using a stand washing tool having a first washing member formed to a first height position and a second washing member formed to a second height position lower than the first height position. The washing method comprises a first washing member inserting step of inserting the first washing member into a gap between a stand storage wall section of the endoscope and the treatment tool stand; a second washing member abutting step of making the second washing member abut against a treatment tool guide surface of the treatment tool stand; and a stand washing tool moving step of moving the stand washing tool along the treatment tool guide surface in a state where the first washing member is inserted into the gap and the second washing member is made to abut against the treatment tool guide surface.

20 Claims, 13 Drawing Sheets

(51) Int. Cl.
*A46B 9/04* (2006.01)
*A61B 1/00* (2006.01)
*A61B 90/70* (2016.01)

(52) U.S. Cl.
CPC ...... *A61B 90/70* (2016.02); *A46B 2200/3073* (2013.01); *A61B 2090/701* (2016.02)

(58) Field of Classification Search
USPC ............................................................ 134/6
See application file for complete search history.

(56) References Cited

U.S. PATENT DOCUMENTS

2006/0162105 A1* 7/2006 Abe ................. A61B 1/122
  15/104.2
2018/0049834 A1* 2/2018 Awadu ................. A61B 1/00

FOREIGN PATENT DOCUMENTS

| | | |
|---|---|---|
| JP | 2002052027 | 2/2002 |
| JP | 2002125929 | 5/2002 |
| JP | 2002-209848 | 7/2002 |
| JP | 2005028030 | 2/2005 |
| JP | 2010201020 | 9/2010 |

OTHER PUBLICATIONS

"Written Opinion of the International Searching Authority (Form PCT/ISA/237) of PCT/JP2016/070146," dated Sep. 27, 2016, with English translation thereof, pp. 1-7.

"Search Report of European Counterpart Application" dated Jun. 29, 2018, p. 1-p. 6.

"Office Action of Japan Counterpart Application," dated Sep. 26, 2018, with English translation thereof, pp. 1-4.

* cited by examiner

METHOD FOR WASHING TREATMENT TOOL STAND

CROSS-REFERENCE TO RELATED APPLICATIONS

This application is a Continuation of PCT International Application No. PCT/JP2016/070146 filed on Jul. 7, 2016, which claims priority under 35 U.S.C. § 119(a) to Japanese Patent Application No. 2015-160472 filed on Aug. 17, 2015. Each of the above applications is hereby expressly incorporated by reference, in their entirety, into the present application.

BACKGROUND OF THE INVENTION

1. Field of the Invention

The present invention relates to a method for washing an endoscope, and particularly, to a method for washing a treatment tool stand provided at a distal end of an endoscope insertion part.

2. Description of the Related Art

In endoscopes, various treatment tools are inserted into a treatment tool insertion port provided in an operating part, and the treatment tools are delivered and used from a treatment tool outlet to a distal end of an endoscope insertion part. For example, a guide wire and a contrast tube are used for duodenoscopes, and treatment tools, such as a puncturing needle, are used for ultrasonic endoscopes. In such treatment tools, it is necessary to change a delivery direction at a distal end in order to perform treatment at a desired position within a subject. For this reason, a treatment tool stand is provided at the distal end as described in JP2010-201020A.

Whenever an endoscope is used for various kinds of inspection and treatment, it is necessary to perform washing and disinfection processing by using a washing liquid and a disinfectant. Particularly, since the frequency at which the distal end of the endoscope insertion part is contaminated with body fluid, blood, or the like during various kinds of inspection and treatment washes is high, even the fine parts of the structure are washed, for example, using a stand washing tool, such as a washing brush.

For example, JP1996-182648A (JP-H08-182648) suggests a washing brush, which has an elongated core (head) coupled to one end of a gripping part (handle) and forms a brush part by erecting brush hairs in one direction on a distal end side of the core, as the stand washing tool that washes the treatment tool stand.

SUMMARY OF THE INVENTION

As the distal end of the endoscope is miniaturized, the treatment tool stand is complicated. For that reason, a small gap is present on the structure between the treatment tool stand and a stand storage wall section, for example, between an outer peripheral part of a root section (a rotating shaft holding section) of the treatment tool stand, and the stand storage wall section.

However, washing the gap around the treatment tool stand is not taken into consideration in the washing brush suggested in JP1996-182648A (JP-H08-182648). For that reason, in order to wash the gap around the treatment tool stand, exclusive washing tools have to be separately prepared, substantial time and effort such as separately using the washing tools for respective sites to be washed are taken, and the washing operation becomes complicated. As a result, substantial time and effort are required for washing the treatment tool stand and the gap therearound.

The invention has been made in view of such circumstances, and an object thereof is to provide a method for washing a treatment tool stand that can efficiently perform the operation of washing the treatment tool stand in a short time without taking substantial time and effort.

In order to achieve the above object, a method for washing a treatment tool stand related to a first aspect of the invention is a method for washing a treatment tool stand of an endoscope, using a stand washing tool having a handle having a distal end, a proximal end, and a longitudinal axis, a head provided on a distal end side of the handle, a first washing member erected in a direction intersecting a reference plane including the longitudinal axis on the head, and a second washing member erected in a direction intersecting the reference plane on the head closer to the handle than the first washing member and provided so as to be parallel to or coincide with the first washing member in a case where the second washing member is projected on a plane perpendicular to the longitudinal axis. The first washing member has a first end opposite to one end on the head side. The second washing member has a second end opposite to one end on the head side. A height position of the first end in a direction orthogonal to the reference plane from the reference plane is a first height position. A height position of the second end in the direction orthogonal to the reference plane from the reference plane is a second height position lower than the first height position. The washing method comprises a first washing member inserting step of inserting the first washing member into a gap between the stand storage wall section of the endoscope and the treatment tool stand; a second washing member abutting step of making the second washing member abut against a treatment tool guide surface of the treatment tool stand; and a stand washing tool moving step of moving the stand washing tool along the treatment tool guide surface in a state where the first washing member is inserted into the gap and the second washing member is made to abut against the treatment tool guide surface.

According to the first aspect, the operation of washing the treatment tool stand is performed in a state where the second washing member is made to abut against the treatment tool guide surface of the treatment tool stand while inserting the first washing member into the gap between the stand storage wall section of the endoscope and the treatment tool stand, by using the stand washing tool in which the first height position of the first washing member is higher than the second height position of the second washing member. Accordingly, simultaneously with the washing of the treatment tool guide surface of the treatment tool stand by the second washing member, it is also possible to wash the gap between the stand storage wall section and the treatment tool stand with the first washing member. As a result, the operation of efficiently washing the treatment tool stand can be performed in a short time without taking substantial time and effort.

A method for washing a treatment tool stand related to a second aspect of the invention is a method for washing a treatment tool stand of an endoscope, using a stand washing tool having a handle having a distal end, a proximal end, and a longitudinal axis, a head provided on a distal end side of the handle, a first washing member erected in a direction intersecting a reference plane including the longitudinal axis on the head, and a second washing member erected in a direction intersecting the reference plane on the head closer to the handle than the first washing member and provided so as to be parallel to the first washing member in a case where the second washing member is projected on a plane perpendicular to the longitudinal axis. The first washing member has a first end opposite to one end on the head side. The second washing member has a second end opposite to one end on the head side. A height position of the first end in a direction orthogonal to the reference plane from the reference plane is a first height position. A height position of the second end in the direction orthogonal to the reference plane from the reference plane is a second height position lower than the first height position. The washing method comprises a first washing member inserting step of inserting the first washing member into a gap between the stand storage wall section of the endoscope and the treatment tool stand; a second washing member abutting step of making the second washing member abut against a back surface opposite to a treatment tool guide surface of the treatment tool stand; and a stand washing tool moving step of moving the stand washing tool along the back surface in a state where the first washing member is inserted into the gap and the second washing member is made to abut against the back surface.

According to the second aspect, the operation of washing the treatment tool stand is performed in a state where the second washing member is made to abut against the back surface of the treatment tool stand while inserting the first washing member into the gap between the stand storage wall section of the endoscope and the treatment tool stand, by using the stand washing tool in which the first height position of the first washing member is higher than the second height position of the second washing member. Accordingly, simultaneously with the washing of the back surface of the treatment tool stand by the second washing member, it is also possible to wash the gap between the stand storage wall section and the treatment tool stand with the first washing member. As a result, the operation of efficiently washing the treatment tool stand can be performed in a short time without taking substantial time and effort.

The method for washing a treatment tool stand related to a third aspect is an aspect based on the first aspect in which, in the first washing member inserting step, the first washing member is inserted into the gap after the treatment tool stand is tilted.

According to the third aspect, since the first washing member is inserted into the gap after the treatment tool stand is tilted, the first washing member is easily inserted into the gap, and it is possible to more efficiently perform the washing operation.

The method for washing a treatment tool stand related to a fourth aspect is an aspect based on the second aspect in which, in the first washing member inserting step, the first washing member is inserted into the gap after the treatment tool stand is raised.

According to the fourth aspect, since the second washing member is inserted into the gap after the treatment tool stand is raised, the second washing member is easily inserted into the gap, and it is possible to more efficiently perform the washing operation.

A method for washing a treatment tool stand related to a fifth aspect of the invention is a method for washing a treatment tool stand of an endoscope, using a stand washing tool having a handle having a distal end, a proximal end, and a longitudinal axis, a head provided on a distal end side of the handle, a first washing member that is erected in a first direction intersecting a reference plane including the longitudinal axis on the head and has a first length in the first direction, a second washing member that is erected in a second direction intersecting the reference plane on the head closer to the handle than the first washing member, is provided so as to be parallel to or coincide with the first washing member in a case where the second washing member is projected on a plane perpendicular to the longitudinal axis, and has a second length shorter than the first length in the second direction. The washing method comprises a first washing member inserting step of inserting the first washing member into a gap between the stand storage wall section of the endoscope and the treatment tool stand; second washing member abutting step of making the second washing member abut against a treatment tool guide surface of the treatment tool stand; and a stand washing tool moving step of moving the stand washing tool along the treatment tool guide surface in a state where the first washing member is inserted into the gap and the second washing member is made to abut against the treatment tool guide surface.

According to the fifth aspect, the operation of washing the treatment tool stand is performed in a state where the second washing member is made to abut against the treatment tool guide surface of the treatment tool stand while inserting the first washing member into the gap between the stand storage wall section of the endoscope and the treatment tool stand, by using the stand washing tool in which the first length of the first washing member in the first direction is higher than the second length of the second washing member in the second direction. Accordingly, simultaneously with the washing of the treatment tool guide surface of the treatment tool stand by the second washing member, it is also possible to wash the gap between the stand storage wall section and the treatment tool stand with the first washing member. As a result, the operation of efficiently washing the treatment tool stand can be performed in a short time without taking substantial time and effort.

A method for washing a treatment tool stand related to a sixth aspect of the invention is a method for washing a treatment tool stand of an endoscope, using a stand washing tool having a handle having a distal end, a proximal end, and a longitudinal axis, a head provided on a distal end side of the handle, a first washing member that is erected in a first direction intersecting a reference plane including the longitudinal axis on the head and has a first length in the first direction, a second washing member that is erected in a second direction intersecting the reference plane on the head closer to the handle than the first washing member, is provided so as to be parallel to or coincide with the first washing member in a case where the second washing member is projected on a plane perpendicular to the longitudinal axis P, and has a second length shorter than the first length in the second direction. The washing method comprises a first washing member inserting step of inserting the first washing member into a gap between the stand storage wall section of the endoscope and the treatment tool stand; second washing member abutting step of making the second washing member abut against a back surface opposite to a treatment tool guide surface of the treatment tool stand; and a stand washing tool moving step of moving the stand washing tool along the back surface in a state where the first washing member is inserted into the gap and the second washing member is made to abut against the back surface.

According to the sixth aspect, the operation of washing the treatment tool stand is performed in a state where the second washing member is made to abut against the back surface of the treatment tool stand while inserting the first washing member into the gap between the stand storage wall section of the endoscope and the treatment tool stand, by using the stand washing tool in which the first length of the first washing member in the first direction is higher than the second length of the second washing member in the second direction. Accordingly, simultaneously with the washing of the back surface of the treatment tool stand by the second washing member, it is also possible to wash the gap between the stand storage wall section and the treatment tool stand with the first washing member. As a result, the operation of efficiently washing the treatment tool stand can be performed in a short time without taking substantial time and effort.

The method for washing a treatment tool stand related to a seventh aspect is an aspect based on the fifth aspect in which, in the first washing member inserting step, the first washing member is inserted into the gap after the treatment tool stand is tilted.

According to the seventh aspect, since the first washing member is inserted into the gap after the treatment tool stand is tilted, the first washing member is easily inserted into the gap, and it is possible to more efficiently perform the washing operation.

The method for washing a treatment tool stand related to an eighth aspect is an aspect based on the sixth aspect in which, in the first washing member inserting step, the first washing member is inserted into gap after the treatment tool stand is raised.

According to the eighth aspect, since the first washing member is inserted into the gap after the treatment tool stand is raised, the first washing member is easily inserted into the gap, and it is possible to more efficiently perform the washing operation.

The method for washing a treatment tool stand related to a ninth aspect is an aspect based on any one of the first to fourth aspects in which the head has a washing member holding surface that holds the first washing member and the second washing member, and the following Conditional Expression (1) is satisfied in a case where a length from the washing member holding surface of the first washing member to the first end is defined as L1 and a length from the washing member holding surface of the second washing member to the second end is defined as L2.

$$L1 > L2 \qquad (1)$$

According to the ninth aspect, since the length L1 from the washing member holding surface of the first washing member to the first end is made longer than the length L2 from the washing member holding surface of the second washing member to the second end, the gap and the guide surface of the treatment tool stand can be simultaneously washed in a state where the second washing member is made to abut against the guide surface of the treatment tool stand while inserting the first washing member into the gap between the stand storage wall section of the endoscope and a treatment tool stand. Therefore, it is possible to efficiently perform the operation of washing the treatment tool stand in a short time without taking substantial time and effort.

The method for washing a treatment tool stand related to a tenth aspect is an aspect based on any one of the first to fourth aspects in which the head has a first washing member holding surface that holds the first washing member and a second washing member holding surface that holds the second washing member, and the following Conditional Expression (2) is satisfied in a case where a height position of the first washing member holding surface in a direction orthogonal to the reference plane from the reference plane is a third height position, a height position of the second washing member holding surface in the direction orthogonal to the reference plane from the reference plane is a fourth height position lower than the third height position, a difference between the third height position and the fourth height position is defined as L3, a length from the first washing member holding surface of the first washing member to the first end is defined as L4, and a length from the second washing member holding surface of the second washing member to the second end is defined as L5.

$$L3 + L4 > L5 \qquad (2)$$

According to the tenth aspect, since the first washing member holding surface is formed to be higher by L3 than the second washing member holding surface, the length L4 from the first washing member holding surface of the first washing member to the first end can be made to be shorter by L3, and the stiffness of the first washing member can be strengthened. Therefore, it is possible to more efficiently perform the operation of washing the treatment tool stand.

The method for washing a treatment tool stand related to an eleventh aspect is an aspect based on any one of the first to tenth aspects in which the stand storage wall section has a first side wall section and a second side wall section that face each other with the treatment tool stand interposed therebetween, and a base wall section provided between a first side wall section and the second side wall section, and the gap is a gap between the base wall section and the treatment tool stand.

According to the eleventh aspect, since the gap is the gap between the base wall section and the treatment tool stand, a surface (the treatment tool guide surface or the back surface) of the treatment tool stand to be washed can be made to abut against the second washing member in a state where the first washing member is inserted into the gap, and the gap and the surface of the treatment tool stand to be washed can be simultaneously washed. Therefore, it is possible to efficiently perform the operation of washing the treatment tool stand in a short time without taking substantial time and effort.

The method for washing a treatment tool stand related to a twelfth aspect is an aspect based on any one of the first to eleventh aspects in which the first washing member is harder than the second washing member.

According to the twelfth aspect, since the first washing member is made to be harder than the second washing member, the first washing member is easily inserted into the gap, and it is possible to more efficiently perform the washing operation.

The method for washing a treatment tool stand related to a thirteenth aspect is an aspect based on the twelfth aspect in which the first washing member is formed of a first material, and the second washing member is formed of a second material softer than the first material.

According to the thirteenth aspect, since the first washing member is formed of a material harder than the second washing member, the first washing member is easily inserted into the gap, and it is possible to more efficiently perform the washing operation.

The method for washing a treatment tool stand related to a fourteenth aspect is an aspect based on any one of the first to twelfth aspects in which the first washing member and the second washing member have a plurality of brush hairs.

The method for washing a treatment tool stand related to a fifteenth aspect is an aspect based on the fourteenth aspect in which the brush hairs of the first washing member are thicker than the brush hairs of the second washing member.

According to the fifteenth aspect, since the brush hairs of the first washing member are made to be thicker than the brush hairs of the second washing member, the first washing member is easily inserted into the gap, and it is possible to more efficiently perform the washing operation.

According to the invention, the operation of washing the treatment tool stand can be performed in a short time without taking substantial time and effort.

DESCRIPTION OF THE PREFERRED EMBODIMENTS

Hereinafter, a preferable embodiment of the invention will be described in detail with reference to the accompanying drawings.

Figure 1:
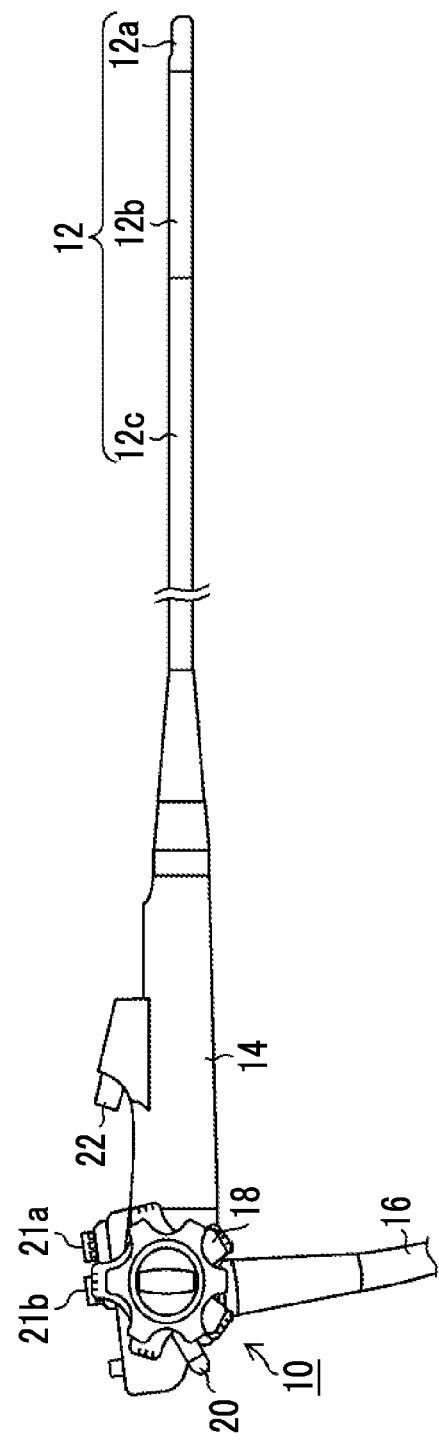
FIG. 1 is an overall configuration view illustrating an example of an endoscope to be washed in the embodiment of the invention.

FIG. 1 is an overall configuration view illustrating an example of an endoscope to be washed in the embodiment of the invention.

An endoscope 10 in FIG. 1 includes an insertion part 12 inserted into a patient's body, an operating part 14 provided continuously with a proximal end of the insertion part 12 and used for gripping the endoscope 10, operating the insertion part 12, and the like, and a universal cord 16 connected the endoscope 10 to system constituent devices, such as a light source device (not illustrated) and a processor device.

The insertion part 12 is configured by coupling a distal end 12a, the bending part 12b, and a flexible part 12c together in order from a distal end side toward a proximal end side. The distal end 12a includes an observation part that captures an image of a region to be observed in the living body and sends the captured image to the processor device connected by the universal cord 16 as an observation image (endoscopic image), an illumination part that radiates illumination light, which propagates through a light guide inside the endoscope 10 from the light source device connected by the universal cord 16, to the region to be observed, and the like. The bending part 12b bends in upward, downward, rightward, and leftward directions through the operation of an angle knob 18 of the operating part 14. The flexible part 12c has flexibility and bends in arbitrary directions along an insertion path of the insertion part 12.

Figure 2:
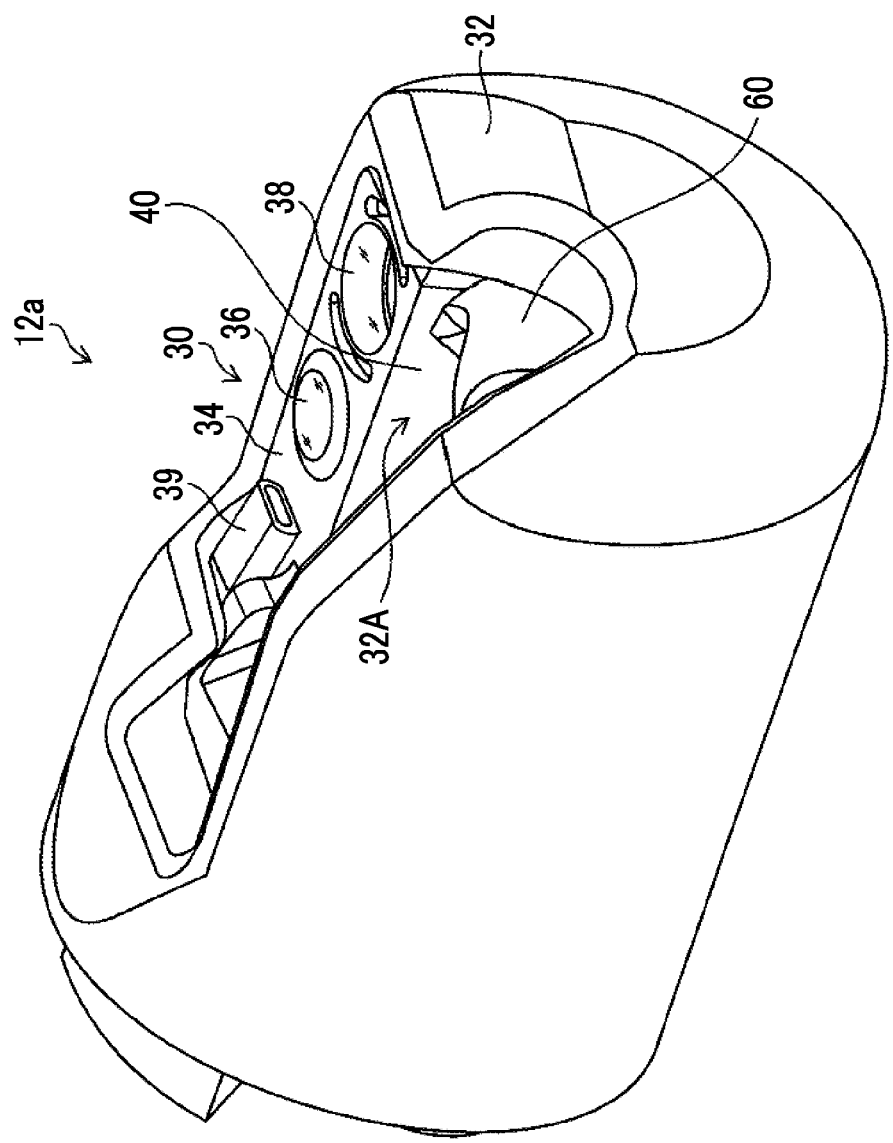
FIG. 2 is an enlarged perspective view illustrating a distal end of the endoscope illustrated in FIG. 1.

FIG. 2 is an enlarged perspective view illustrating the distal end of the endoscope illustrated in FIG. 1. The endoscope 10 of the present embodiment is, for example, a side-view endoscope used as a duodenoscope, and the distal end 12a of FIG. 2 shows a configuration in the side-view endoscope. As illustrated in FIG. 2, the distal end 12a has a distal end main body 30, and a cap 32 that covers the distal end main body 30. An opening window 32A is formed at a position corresponding to an opening on an upper surface side of a stand accommodating slit 40 (to be described below) in a state where the cap 32 is mounted on the distal end main body 30, in the cap 32. The cap 32 is made of materials with an elastic force, for example, silicone rubber. In the endoscope 10 of the present embodiment, the cap 32 is bonded to the distal end main body 30.

As illustrated in FIG. 2, the distal end 12a is provided with a flat surface 34 substantially parallel to a longitudinal axis that is an axis of the insertion part 12, and the flat surface 34 is provided with an observation window 36 and an illumination window 38.

The observation window 36 is a constituent element of the observation part that acquires the image of the region to be observed that is present on a lateral side (radial direction) with respect to the longitudinal axis of the insertion part 12, and takes object light from the region to be observed on the lateral side into an optical system (an imaging lens and the like) as another constituent element of the observation part, and image pick-up means. The illumination window 38 is a constituent element of the illumination part mounted on the distal end 12a, and radiates illumination light, which is emitted from a light-emitting part that is another constituent element of the illumination part, that is, from a light-emitting part provided at a terminal part of the light guide that propagates the light from the light source device, to the region to be observed.

Figure 3:
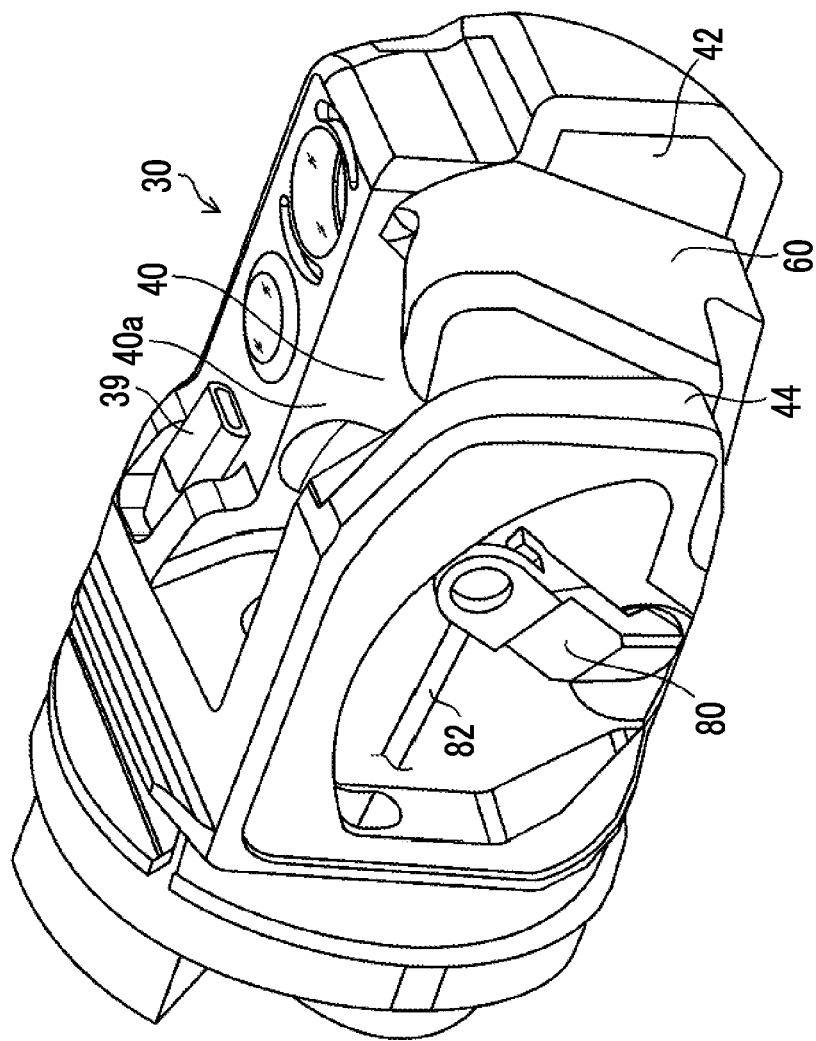
FIG. 3 is a perspective view illustrating a state where a cap is detached from the distal end illustrated in FIG. 2.

FIG. 3 is a perspective view illustrating a state where the cap is detached from the distal end illustrated in FIG. 2. In the distal end main body 30, the stand accommodating slit 40 surrounded by a first side wall section 42, a second side wall section 44, and a base wall section 46 (refer to FIG. 4, hereinafter these are also collectively referred to as a stand storage wall section 48) is provided on a right side as seen from the proximal end side of the distal end 12a of the flat surface 34, and the stand accommodating slit 40 is provided with the treatment tool stand 60 (hereinafter also simply referred to as a stand 60). The stand accommodating slit 40 communicates with a treatment tool inlet 22 (refer to FIG. 1) of the operating part 14 through a treatment tool insertion channel inserted through which the insertion part 12 is inserted, and a treatment tool inserted from the treatment tool inlet 22 is guided to the stand accommodating slit 40 via a treatment tool outlet (not illustrated).

The stand 60 bends a traveling direction of the treatment tool led to the stand accommodating slit 40 via the treatment tool outlet, and guided the treatment tool in a direction toward an opening 40a on the upper surface side of the stand accommodating slit 40.

Additionally, the stand 60 is raised and tilted (rotated) in a direction (raised direction) in which the stand 60 is raised or in a direction (tilted direction) in which the stand 60 is tilted, through the operation of a raising operating lever 20 (refer to FIG. 1) of the operating part 14, and changes a delivery direction (delivery angle) of the treatment tool led to the stand accommodating slit 40 via the treatment tool outlet.

Specifically, the stand 60 is coupled to the raising lever 80 via a rotating shaft (not illustrated) with the second side wall section 44 therebetween, and a distal end of an operation wire 82 is coupled to a distal end of the raising lever 80. The operation wire 82 is inserted through the insertion part 12 and is coupled to the raising operating lever 20 of the operating part 14.

Accordingly, the operation wire 82 is pushed and pulled through the operation of the raising operating lever 20 and thus the raising lever 80 and the rotating shaft (not illustrated) are rotated, and through this rotation, the stand 60 is rotated and the stand 60 is raised and tilted. In addition, a stand raising mechanism that rotates the rotating shaft is not limited to that of the present embodiment that pushes and pulls the raising lever 80 with the operation wire 82.

In addition, an air/water supply nozzle 39, which performs air supply and water supply to the observation window 36 in a switchable manner through the operation of an air/water supply button 21a (refer to FIG. 1) of the operating part 14, is provided in the vicinity the observation window 36 of the flat surface 34. Additionally, a suction channel is connected to the treatment tool insertion channel within the insertion part 12, and suction from the stand accommodating slit 40 is performed through the operation of a suction button 21b (refer to FIG. 1) of the operating part 14.

Figure 4:
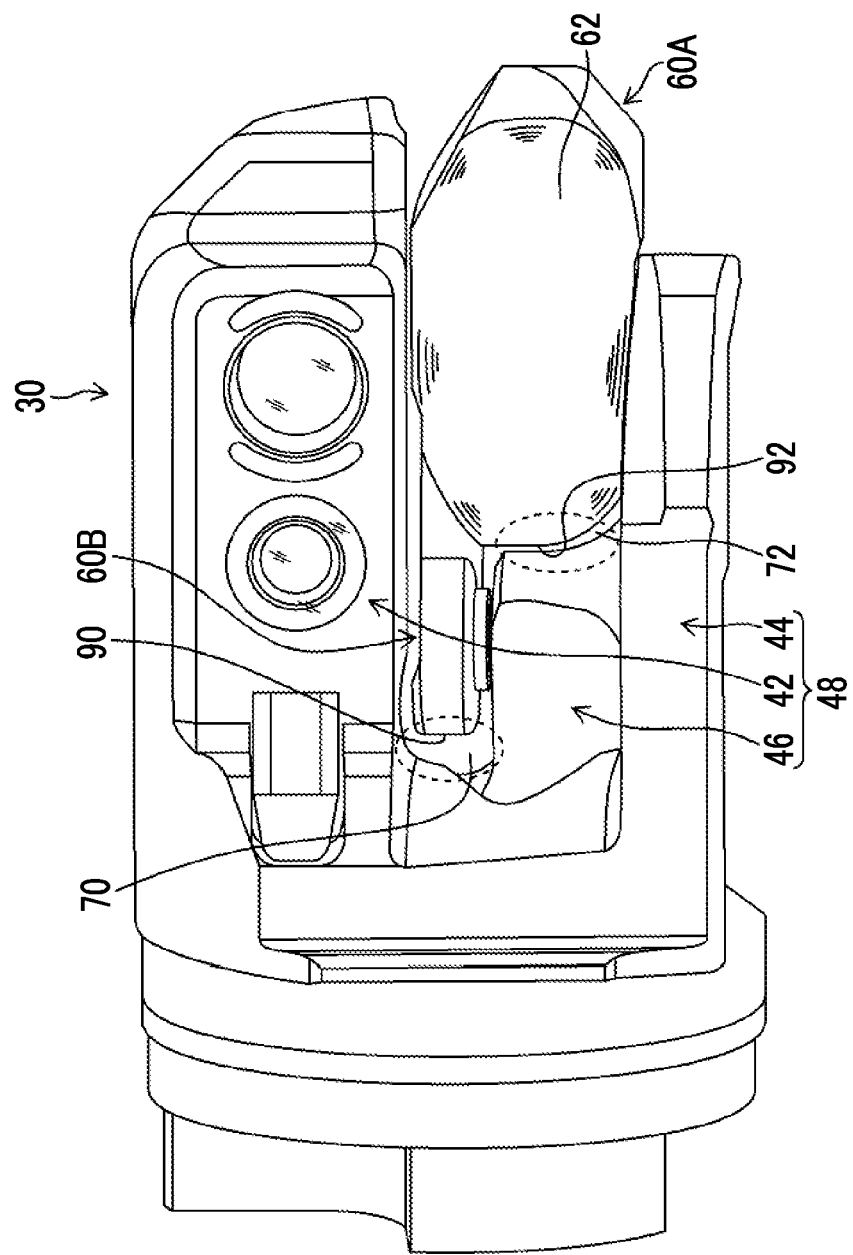
FIG. 4 is a top view of a distal end main body illustrated in FIG. 3.
Figure 5:
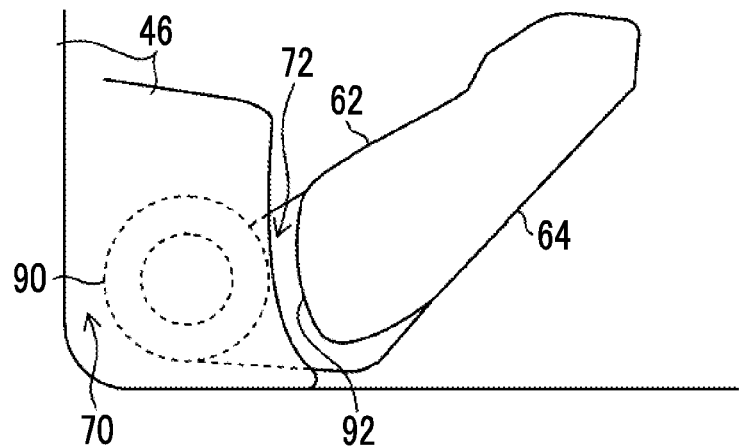
FIG. 5 is a schematic view of a stand as seen from a side surface side.

FIG. 4 is a top view (a view of the distal end main body 30 as seen from the upper surface side (flat surface 34 side)) of the distal end main body 30 illustrated in FIG. 3. Additionally, FIG. 5 is a schematic view of the stand 60 as seen from the side surface side (second side wall section 44 side).

As illustrated in FIG. 4, the stand 60 is composed of a stand main body section 60A, and a rotating shaft holding section 60B provided continuously with a proximal end of the stand main body section 60A.

The stand main body section 60A has almost the same width as the stand accommodating slit 40, and an upper surface part thereof is provided with a treatment tool guide surface 62 for guiding the treatment tool delivered from the treatment tool outlet in a predetermined direction. The stand main body section 60A has a swelling shape that swells to the second side wall section 44 side, and a proximal end side of the swelling portion thereof is provided with a rear end surface 92 that faces the base wall section 46 with a predetermined gap therefrom.

The rotating shaft holding section 60B is a part that holds the rotating shaft of the stand 60, one end thereof is combined with the stand main body section 60A the other end thereof has a base part end surface 90 consisting of a circular-arc outer peripheral surface, and the rotating shaft of the stand 60 is provided inside the rotating shaft holding section.

As illustrated in FIG. 4, a predetermined clearance (gap) is provided between the stand 60 and the stand storage wall section 48 such that the stand 60 is rotatable around the rotating shaft in a state where the stand 60 is stored in the stand storage wall section 48.

Since s side surface part of the stand 60 can be easily exposed to the outside of the stand accommodating slit 40 by raising and tilting the stand 60, washing is relatively easy, whereas a root section (rotating shaft holding section 60B) of the stand 60, a gap 70 formed between the base part end surface 90 of the rotating shaft holding section 60B of the stand 60 and the stand storage wall section 48, and a gap 72 formed between the rear end surface 92 of the stand main body section 60A and the stand storage wall section 48 are small, and as illustrated in FIG. 5, the gap 70 between the base part end surface 90 of the rotating shaft holding section 60B of the stand 60 and the stand storage wall section 48 is structurally located at a deep part of the stand accommodating slit 40, inserting the stand washing tool is troublesome, and washing takes substantial time and effort.

Thus, in the washing method the present embodiment, as will be described below in detail, the gap 70 or 72 provided between the treatment tool stand 60 and the stand storage wall section 48 can be simultaneously washed together with the washing of a surface (the treatment tool guide surface 62 or a back surface 64) to be washed of the treatment tool stand 60, using a stand washing tool 100A having washing members 106 and 108 (a first washing member 106 and a second washing member 108) having mutually different heights. As a result, it is possible to efficiently perform the operation of washing the treatment tool stand 60 in a short time without taking substantial time and effort. Details will be described below.

Figure 6:
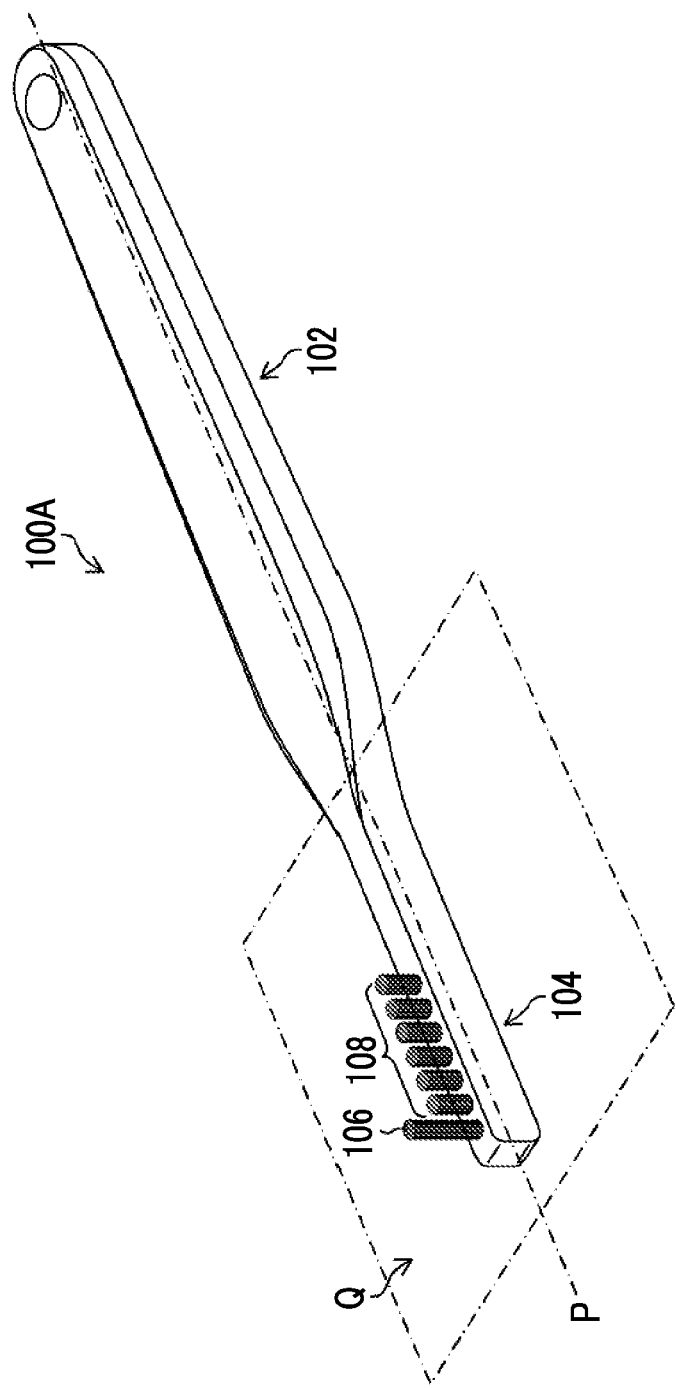
FIG. 6 is a perspective view illustrating a stand washing tool used in the present embodiment.
Figure 7:
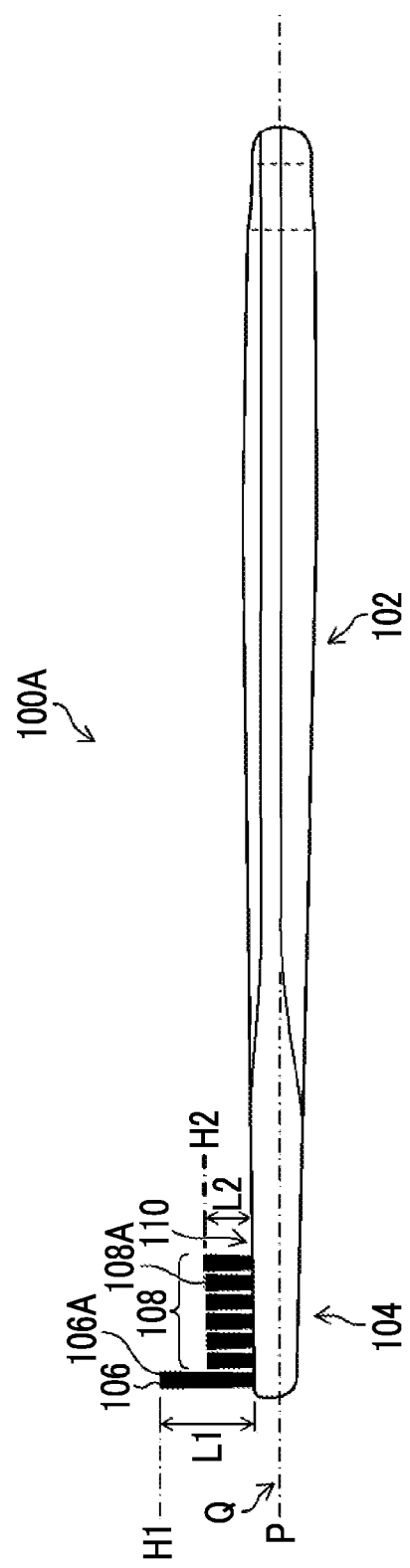
FIG. 7 is a side view of the stand washing tool illustrated in FIG. 6.
Figure 8:
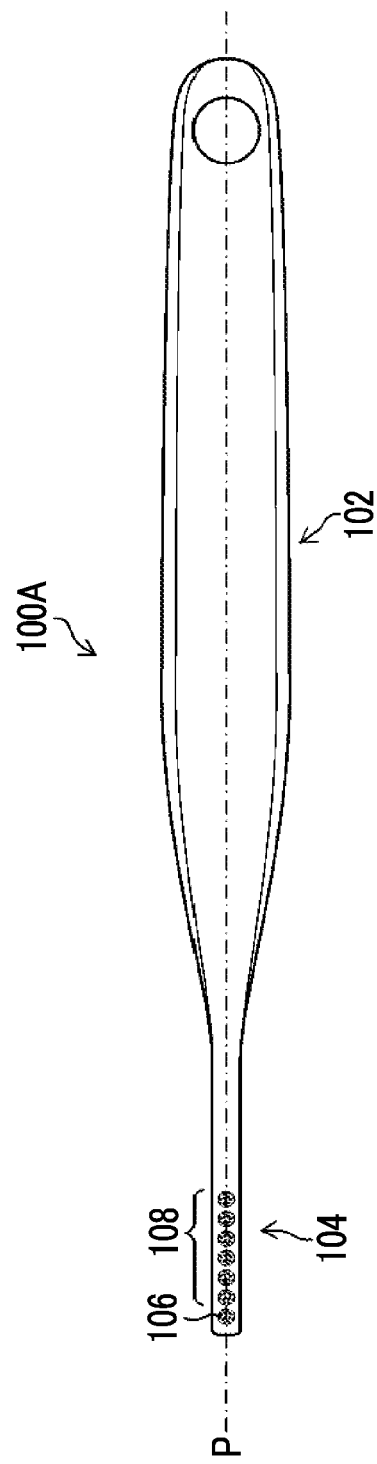
FIG. 8 is a top view of the stand washing tool illustrated in FIG. 6.

The stand washing tool 100A used in the present embodiment is illustrated in FIGS. 6, 7, and 8. FIG. 6 is a perspective view, FIG. 7 is a side view, and FIG. 8 is a top view.

As illustrated in FIG. 6 to FIG. 8, the stand washing tool 100A of the present embodiment has a handle 102 for gripping the stand washing tool 100A, and a head 104 from which the washing members 106 and 108 are erected.

The handle 102 has a distal end, a proximal end, and a longitudinal axis P, and the head 104 is provided on the distal end side of the handle 102. As illustrated in FIG. 8, the width of the head 104 in a direction perpendicular to the longitudinal axis P is narrower than the width of the handle 102 in the direction perpendicular to the longitudinal axis P. Accordingly, the head 104 is easily inserted into the stand accommodating slit 40, and the washing efficiency of the stand 60 and the gap 70 or 72 therearound can be improved. In addition, the width of the head 104 in the direction perpendicular to the longitudinal axis P is determined to be an optimal value in accordance with the dimension (width) of the distal end main body 30 or the stand accommodating slit 40.

The head 104 has the first washing member 106 erected on the distal end side of the head 104, and the second washing member 108 that is adjacent to the first washing member 106 and is erected closer to the handle side than the first washing member 106. In the present embodiment, the first washing member 106 and the second washing member 108 are formed by using a plurality of brush hairs of the same material and the same thickness.

In addition, as will be described below, brush hairs of different materials may be used for the first washing member 106 and the second washing member 108. Additionally, materials other than the brush hairs may be used for the first washing member 106 and the second washing member 108, or the first washing member 106 and the second washing member 108 may be made of different materials.

Additionally, in the stand washing tool 100A of the present embodiment, as illustrated in FIG. 7, the first washing member 106 is longer than the second washing member 108 in order to facilitate insertion of the first washing member 106 into the gaps 70 and 72 provided between the stand 60 and the stand storage wall section 48.

Here, a length relationship between the first washing member 106 and the second washing member 108 will be described in detail.

As illustrated in FIG. 6, a plane including the longitudinal axis P of the handle 102 is defined as a reference plane Q. As illustrated in FIG. 7, in a case where the height position of the first washing member 106 in the direction perpendicular to the reference plane Q from the reference plane Q is defined as a first height position H1 and the height position of the second washing member 108 in the direction perpendicular to the reference plane Q from the reference plane Q is defined as a second height position H2, the lengths of the first washing member 106 and the second washing member 108 are specified such that the first height position H1 is higher than the second height position H2.

Moreover, details will be described. As illustrated in FIG. 7, in the present embodiment, the head 104 of the stand washing tool 100A has a washing member holding surface 110 from which the first washing member 106 and the second washing member 108 are erected. Additionally, the first washing member 106 and the second washing member 108 respectively have a first end 106A and a second end 108A as the other ends opposite to one ends on the head side (washing member holding surface side).

Here, in a case where the length from the washing member holding surface 110 to the first end 106A is defined as L1 and the length from the washing member holding surface 110 to the second end 108A is defined as L2, the following Expression (3) is satisfied.

$$L1 > L2 \quad (3)$$

That is, in the present embodiment, the first washing member 106 and the second washing member 108 are held on the washing member holding surface 110 substantially parallel to the reference plane Q, and the length L1 of the first washing member 106 and the length L2 of the second washing member 108 are specified so as to satisfy the above Expression (3). By satisfying such a relationship, the first washing member 106 is formed to be longer than the second washing member 108. Thus, in a case where the surface (the treatment tool guide surface 62 or the back surface 64) to be washed of the stand 60 is washed, the first washing member 106 is easily inserted into the gap 70 or 72 (refer to FIG. 4) between the stand 60 and the stand storage wall section 48, and the second washing member 108 can be made to abut against the surface to be washed.

Additionally, in the stand washing tool 100A of the present embodiment, as illustrated in FIG. 8, the first washing member 106 and the second washing member 108 are erected on the same straight line along the longitudinal axis P so that the surface (the treatment tool guide surface 62 or the back surface 64) to be washed and the gap 70 or 72 between the stand 60 and the stand storage wall section 48 can be simultaneously washed. That is, the first washing member 106 and the second washing member 108 are erected such that the first washing member 106 and the second washing member 108 coincide with each other in a case where the first washing member 106 and the second washing member 108 are projected on a plane perpendicular to the longitudinal axis P.

Therefore, it is possible to efficiently perform washing in a state where the first washing member 106 is inserted up to a deep part of a gap on an extension line of the surface to be washed, while washing the surface to be washed with the second washing member 108. In addition, in the present embodiment, the first washing member 106 and the second washing member 108 are disposed side by side in one row on the same straight line. However, the invention is not limited to this. For example, the second washing member 108 may be disposed in multiple rows along the longitudinal axis P of the head 104. That is, the first washing member 106 and the second washing member 108 are erected so as to be parallel to each other in a case where the first washing member 106 and the second washing member 108 are projected on the plane perpendicular to the longitudinal axis P. According to this aspect, it is possible to improve the washing efficiency of the surfaces (the treatment tool guide surface 62 and the back surface 64) to be washed while washing the gap 70 or 72 between the stand 60 and the stand storage wall section 48.

Next, a procedure of the washing method of the present embodiment will be described for respective surfaces to be washed.

Figure 9A:
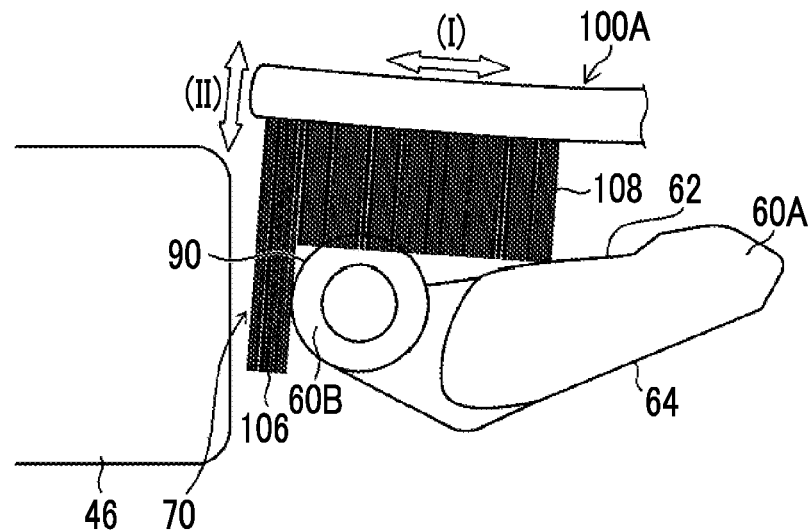
FIG. 9A is a schematic view illustrating a state where the stand is washed using the stand washing tool.
Figure 9B:
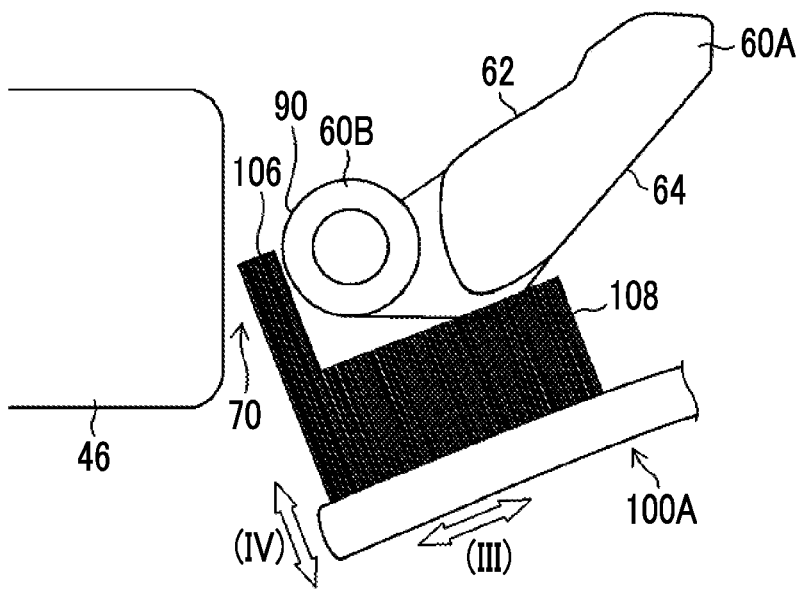
FIG. 9B is a schematic view illustrating a state where the stand is washed using the stand washing tool.
Figure 9C:
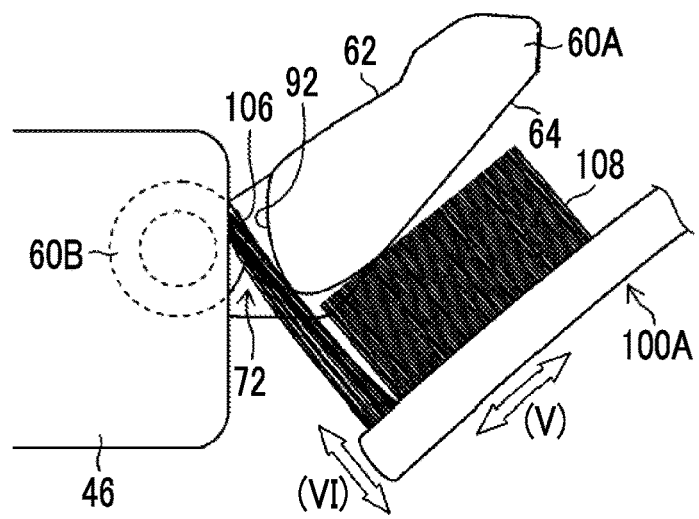
FIG. 9C is a schematic view illustrating a state where the stand is washed using the stand washing tool.

FIGS. 9A to 9C are schematic views illustrating states where the stand is washed using the stand washing tool, and illustrating positional relationships between the stand washing tool 100A and the stand 60 in a case where the respective surfaces to be washed are washed.

Figure 10:
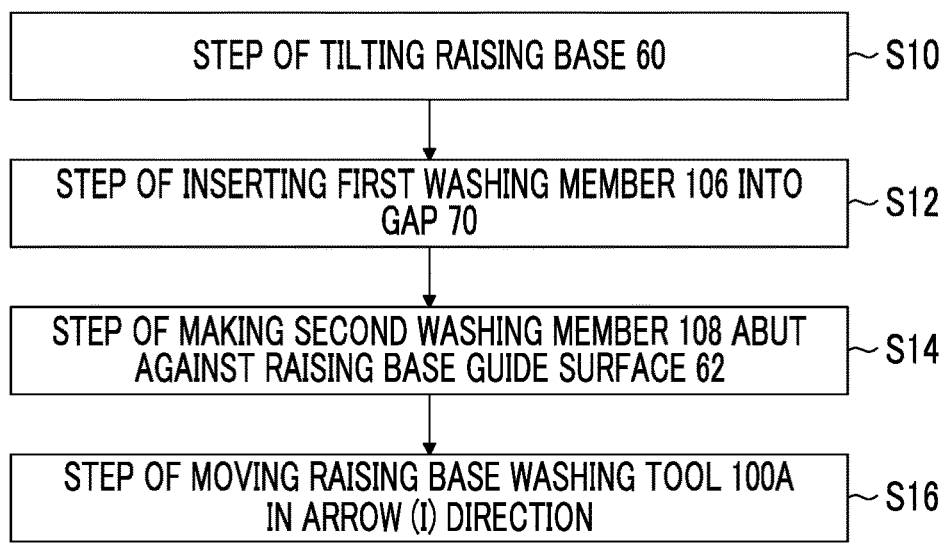
FIG. 10 is a flowchart illustrating a procedure of the washing method related to the present embodiment.

First, FIG. 9A will be described. The surfaces to be washed herein are the treatment tool guide surface 62, the base part end surface 90 of the rotating shaft holding section 60B of the stand 60, and the gap 70 between the base part end surface 90 and the base wall section 46. Hereinafter, the procedure of the washing will be described, referring to FIG. 9A and a flowchart of FIG. 10.

Step S10: Stand Tilting Step

First, the stand 60 is tilted. By doing so, an opening region of the gap 70 between the rotating shaft holding section 60B of the stand 60 and the base wall section 46 can be expanded, and the insertion of the first washing member 106 to be described below becomes easy.

Step S12: First Washing Member Inserting Step

Next, the first washing member 106 is inserted into the gap 70. In this case, in a case where the first washing member 106 is inserted while being moved forward and backward in an insertion direction, the first end 106A of the first washing member 106 can be made to reach a deep part of the gap 70 while effectively removing dirt on the gap 70, for example, dirt adhering to the base part end surface 90 or the base wall section 46.

Step S14: Second Washing Member Abutting Step

The second washing member 108 is made to abut against the treatment tool guide surface 62 while maintaining a state where the above-described first washing member 106 is inserted. By doing in this way, in Step S16 to be described below, the gap 70 and the treatment tool guide surface 62 can be simultaneously washed. In addition, in the second washing member 108, a portion of the second end 108A may abut against the treatment tool guide surface 62, or all the second end 108A may abut against the treatment tool guide surface 62.

Step S16: Washing Tool Moving Step

With the states of the aforementioned first washing member 106 and second washing member 108 maintained, the stand washing tool 100A is moved in a longitudinal axis P direction (an arrow (I) direction of FIG. 9A) of the handle 102.

By doing so, since the first washing member 106 moves in the insertion direction (an arrow (II) direction of FIG. 9A), the gap 70 and the base part end surface 90 of the rotating shaft holding section 60B can be washed, and since the second washing member 108 moves in the longitudinal axis P direction (the arrow (I) direction of FIG. 9A) of the handle 102, the treatment tool guide surface 62 can be washed.

Therefore, the treatment tool guide surface 62, the base part end surface 90 of the rotating shaft holding section 60B of the stand 60, and the gap 70 between the base part end surface 90 and the base wall section 46 can be simultaneously washed.

As described above, the stand 60 and its periphery can be efficiently washed by using the stand washing tool 100A in a short time without taking substantial time and effort.

In addition, in the above-described procedure, the first washing member 106 is inserted into the gap 70 after the stand 60 is tilted. However, the invention is not limited to this, and in a case where the first washing member 106 can be inserted into the gap 70, it is not necessary to tilt the stand 60.

Additionally, in the above-described procedure, the second washing member 108 is made to abut against the treatment tool guide surface 62 after the first washing member 106 is inserted into the gap 70. However, the invention is not limited to this, and the first washing member 106 may be inserted into the gap 70 after the second washing member 108 is made to abut against the treatment tool guide surface 62.

Figure 11:
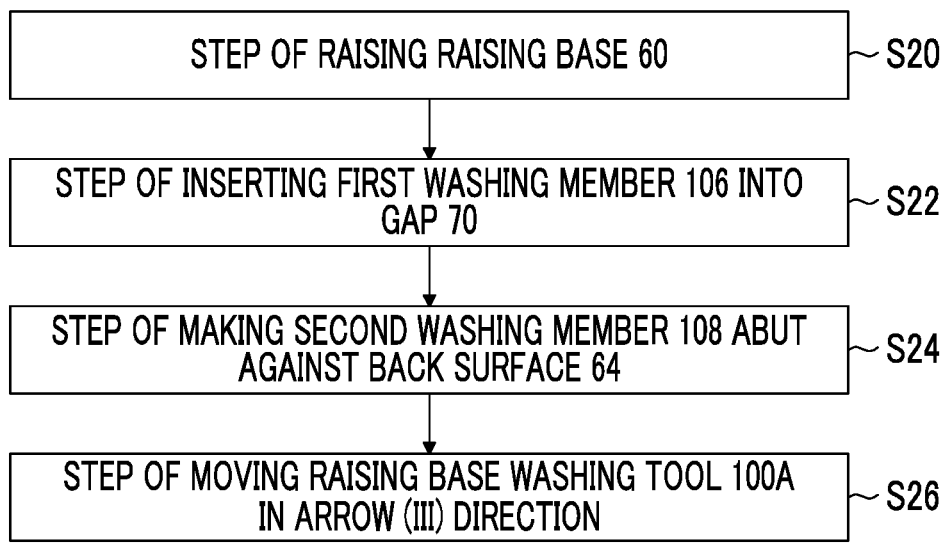
FIG. 11 is a flowchart illustrating a procedure of the washing method related to the present embodiment.

Next, FIG. 9B will be described. The surfaces to be washed herein are the back surface 64 opposite to the treatment tool guide surface 62 of the treatment tool stand 60, the base part end surface 90 of the rotating shaft holding section 60B of the stand 60, and the gap 70 between the base part end surface 90 and the base wall section 46. Hereinafter, the procedure of the washing will be described, referring to FIG. 9B and a flowchart of FIG. 11.

Step S20: Stand Raising Step

First, the stand 60 is raised. By doing so, the opening region of the gap 70 between the rotating shaft holding section 60B of the stand 60 and the base wall section 46 can be expanded, and the insertion of the first washing member 106 to be described below becomes easy.

Step S22: First Washing Member Inserting Step

Next, the first washing member 106 is inserted into the gap 70. In this case, in a case where the first washing member 106 is inserted while being moved forward and backward in the insertion direction, the first end 106A of the first washing member 106 can be made to reach the deep part of the gap 70 while effectively removing dirt on the gap 70, for example, dirt adhering to the base part end surface 90 or the base wall section 46.

Step S24: Second Washing Member Abutting Step

The second washing member 108 is made to abut against the back surface 64 while maintaining the state where the above-described first washing member 106 is inserted. By doing so, in Step S26 to be described below, the gap 70 and the back surface 64 can be simultaneously washed. In addition, a portion of the second end 108A of the second washing member 108 may abut against the back surface 64, or all the second end 108A of the second washing member 108 may abut against the back surface 64.

Step S26: Washing Tool Moving Step

With the states of the aforementioned first washing member 106 and second washing member 108 maintained, the stand washing tool 100A is moved in the longitudinal axis P direction (an arrow (III) direction of FIG. 9B) of the handle 102.

By doing so, since the first washing member 106 moves in the insertion direction (an arrow (IV) direction of FIG. 9B), the gap 70 and the base part end surface 90 of the rotating shaft holding section 60B can be washed, and since the second washing member 108 moves in the longitudinal axis P direction (the arrow (III) direction of FIG. 9B) of the handle 102, the back surface 64 can be washed.

Therefore, the back surface 64, the base part end surface 90 of the rotating shaft holding section 60B of the stand 60, and the gap 70 between the base part end surface 90 and the base wall section 46 can be simultaneously washed.

As described above, the stand 60 and its periphery can be efficiently washed by using the stand washing tool 100A in a short time without taking substantial time and effort.

In addition, in the above-described procedure, the first washing member 106 is inserted into the gap 70 after the stand 60 is raised. However, the invention is not limited to this, and in a case where the first washing member 106 can be inserted into the gap 70, it is not necessary to raise the stand 60.

Additionally, in the above-described procedure, the second washing member 108 is made to abut against the back surface 64 after the first washing member 106 is inserted into the gap 70. However, the invention is not limited to this, and the first washing member 106 may be inserted into the gap 70 after the second washing member 108 is made to abut against the back surface 64.

Figure 12:
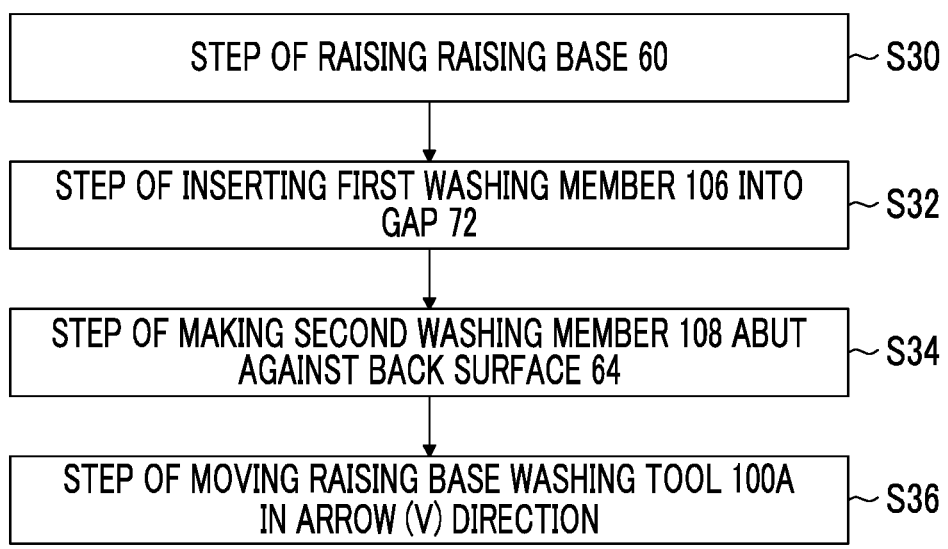
FIG. 12 is a flowchart illustrating a procedure of the washing method related to the present embodiment.

Finally, FIG. 9C will be described. The surfaces to be washed herein are the back surface 64, the rear end surface 92 of the stand main body section 60A of the stand 60, and the gap 72 between the rear end surface 92 and the base wall section 46. Hereinafter, the procedure of the washing will be described, referring to FIG. 9C and a flowchart of FIG. 12.

Step S30: Stand Raising Step

First, the stand 60 is raised. By doing so, the opening region of the gap 72 between the rear end surface 92 of the stand main body section 60A of the stand 60 and the base wall section 46 can be expanded, and the insertion of the first washing member 106 to be described below becomes easy.

Step S32: First Washing Member Inserting Step

Next, the first washing member 106 is inserted into the gap 72. In this case, in a case where the first washing member 106 is inserted while being moved forward and backward in the insertion direction, the first end 106A of the first washing member 106 can be made to reach the deep part of the gap 72 while effectively removing dirt on the gap 72, for example, dirt adhering to the rear end surface 92 or the base wall section 46.

Step S34: Second Washing Member Abutting Step

The second washing member 108 is made to abut against the back surface 64 while maintaining the state where the above-described first washing member 106 is inserted. By doing so, in Step S36 to be described below, the gap 72 and the back surface 64 can be simultaneously washed. In addition, a portion of the second end 108A of the second washing member 108 may abut against the back surface 64, or all the second end 108A of the second washing member 108 may abut against the back surface 64.

Step S36: Washing Tool Moving Step

With the states of the aforementioned first washing member 106 and second washing member 108 maintained, the stand washing tool 100A is moved in the longitudinal axis P direction (an arrow (V) direction of FIG. 9C) of the handle 102.

By doing so, since the first washing member 106 moves in the insertion direction (an arrow (VI) direction of FIG. 9C), the gap 72 and the rear end surface 92 of the rotating shaft holding section 60B can be washed, and since the second washing member 108 moves in the longitudinal axis P direction (the arrow (V) direction of FIG. 9C) of the handle, the treatment tool guide surface 62 can be washed.

Therefore, the back surface 64, the rear end surface 92 of the stand 60, and the gap 72 between the rear end surface 92 and the base wall section 46 can be simultaneously washed.

As described above, the stand 60 and its periphery can be efficiently washed by using the stand washing tool 100A in a short time without taking substantial time and effort.

In addition, in the above-described washing procedure, the first washing member 106 is inserted into the gap 72 after the stand 60 is raised. However, the invention is not limited to this, and in a case where the first washing member 106 can be inserted into the gap 72, it is not necessary to raise the stand 60.

Additionally, in the above-described procedure, the second washing member 108 is made to abut against the back surface 64 after the first washing member 106 is inserted into the gap 72. However, the invention is not limited to this, and the first washing member 106 may be inserted into the gap 72 after the second washing member 108 is made to abut against the back surface 64.

As described above, according to this embodiment, the stand 60 is washed by using the stand washing tool 100A in which the first height position H1 of the first end 106A of the first washing member 106 is higher than the second height position H2 of the second end 108A of the second washing member 108. Accordingly, the surface (the treatment tool guide surface 62 or the back surface 64) to be washed of the stand 60 and the gap 70 or 72 therearound can be washed efficiently in a short time without taking substantial time and effort.

In addition, in the above-described embodiment, the gaps to be washed are the gaps 70 and 72 between the stand 60 and the base wall section 46. However, the invention is not limited to this, and the gaps to be washed may be a gap between the stand 60 and the first side wall section 42 or a gap between the stand 60 and the second side wall section 44.

Additionally, in the above-described embodiment, the stand washing tool 100A has a configuration described in FIG. 6 to FIG. 8. However, it is also possible to adopt other configurations.

First Modification Example

Figure 13:
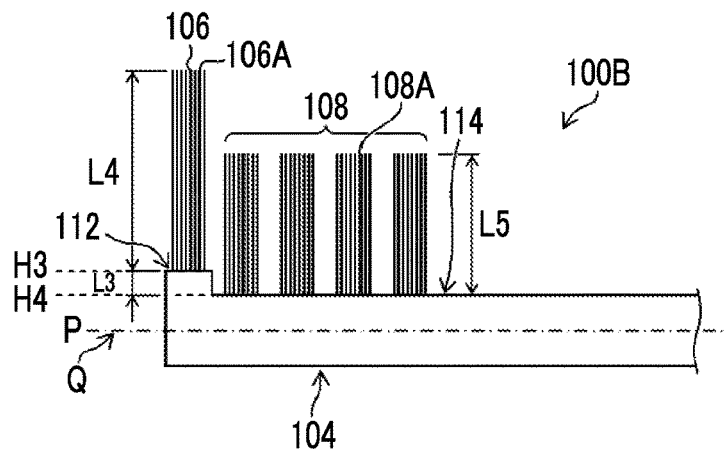
FIG. 13 is a schematic view illustrating the configuration of a stand washing tool as a first modification example.

FIG. 13 is a schematic view illustrating the configuration of a stand washing tool 100B as a first modification example. In FIG. 13, elements that are the same as or similar to those in FIG. 6 to FIG. 8 will be designated by the same reference signs, and the description thereof will be omitted.

As illustrated in FIG. 13, the first washing member 106 and the second washing member 108 being erected on the head 104 of the stand washing tool 100B as the first modification example is the same as that of the above-described embodiment. The first washing member 106 and the second washing member 108 in the first modification example are formed by using a plurality of brush hairs.

In the first modification example, the head 104 has a first washing member holding surface 112 from which the first washing member 106 is erected, and a second washing member holding surface 114 from which the second washing member 108 is erected, and the washing member holding surfaces 112 and 114 are provided at mutually different height positions. That is, the head 104 is configured to have a step between the first washing member holding surface 112 and the second washing member holding surface 114.

Here, a positional relationship between the first washing member holding surface 112 and the second washing member holding surface 114, a length relationship between the first washing member 106 and the second washing member 108, and their correlations will be described in detail.

As illustrated in FIG. 13, in a case where the plane including the longitudinal axis P of the handle 102 is defined as the reference plane Q (refer to FIG. 6), the first washing member holding surface 112 and the second washing member holding surface 114 are provided substantially parallel to the reference plane Q. In a case where the height position of the first washing member holding surface 112 in the direction perpendicular to the reference plane Q from the reference plane Q is defined as a third height position H3 and the height position of the second washing member holding surface 114 in the direction perpendicular to the reference plane Q from the reference plane Q is defined as a fourth height position H4, the first washing member holding surface 112 and the second washing member holding surface 114 are provided such that the third height position H3 is higher by L3 than the fourth height position H4 (a difference between the third height position H3 and the fourth height position H4 is L3).

Next, the lengths of the first washing member 106 and the second washing member 108 will be described. The first washing member 106 has the first end 106A that is the other end opposite to one end on the head side (first washing member holding surface 112 side). Additionally, the second washing member 108 has the second end 108A that is the other end opposite to one end on the head side (second washing member holding surface 114 side).

Here, in a case where the length from the first washing member holding surface 112 of the first washing member 106 to the first end 106A is defined as L4 and the length from the second washing member holding surface 114 of the second washing member 108 to the second end 108A is defined as L5, the following Conditional Expression (4) is satisfied.

$$L3+L4>L5 \qquad (4)$$

The left side of Conditional Expression (4) is the height position H5 from the second washing member holding surface 114 (a surface used as reference) of the first end 106A of the first washing member 106, the right side thereof is the height position H6 from the second washing member holding surface 114 (a surface used as reference) of the second end 108A of the second washing member 108, and Conditional Expression (4) shows that the height position H5 of is higher than the height position H6.

That is, also in the stand washing tool 100B as the first modification example, the height position of the first end 106A of the first washing member 106 is provided at a position higher than the height position of the second end 108A of the second washing member 108. Thus, the surfaces to be washed can be washed by the washing method described FIG. 9A to FIG. 9C, similar to the stand washing tool 100A used in the washing method of the above-described embodiment. Hence, also in the first modification example, similar to the above-described embodiment, it is possible to efficiently perform the operation of washing the treatment tool stand in a short time without taking substantial time and effort.

Additionally, according to the stand washing tool 100B as the first modification example, since the first washing member holding surface 112 and the second washing member holding surface 114 of the head 104 are configured to have a step of the height L3 (that is, since the first washing member holding surface 112 is provided at a position higher than the second washing member holding surface 114, the length of the first washing member 106 can be made shorter compared to that of the stand washing tool 100A of the above-described embodiment. Accordingly, since the stiffness of the first washing member 106 becomes strong, in a case where the treatment tool stand 60 is inserted, the first washing member 106 is easily inserted into the gap 70 or 72, and it is possible to make the first washing member 106 easily enter the deep part of the gap 70 or 72. Hence, the operation of washing the treatment tool stand 60 can be more efficiently performed.

Second Modification Example

Figure 14:
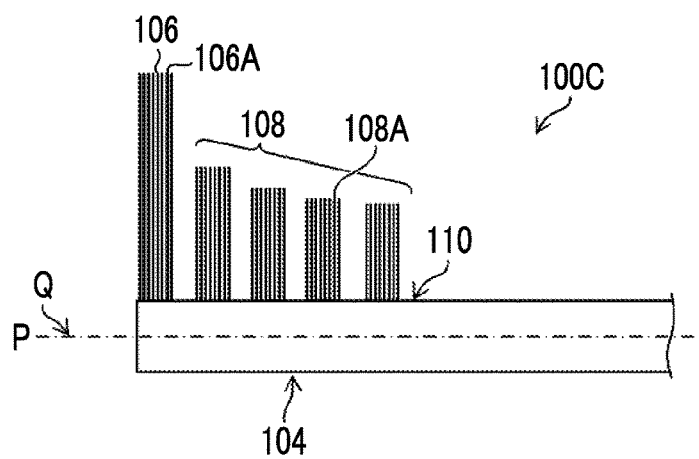
FIG. 14 is a schematic view illustrating the configuration of a stand washing tool as a second modification example.

FIG. 14 is a schematic view illustrating the configuration of a stand washing tool 100C as a second modification example. In FIG. 14, elements that are the same as or similar to those in FIG. 6 to FIG. 8 will be designated by the same reference signs, and the description thereof will be omitted. The first washing member 106 and the second washing member 108 in the second modification example are formed by using a plurality of brush hairs.

As illustrated in FIG. 14, the stand washing tool 100C as the second modification example is the same as that of the above-described embodiment in that the length of the first washing member 106 is longer than the length of the second washing member 108. However, the length of the second washing member 108 becomes shorter stepwise toward the longitudinal axis P proximal end side of the handle 102.

That is, in the stand washing tool 100C as the second modification example, in order to easily insert the first washing member 106 disposed on the distal end side of the head 104 into the gap 70 or 72, the length of the first washing member 106 is made to be longer than the length of the second washing member 108, while the height position of the second end 108A of the second washing member 108 is configured such that the length thereof varies in the longitudinal axis P direction in conformity with the shapes of the surfaces to be washed. For example, as illustrated in FIG. 14, in a case where the length becomes shorter stepwise toward the longitudinal axis P proximal end side, the second washing member 108 is easily made to abut against a convex surface to be washed like the back surface 64 of the treatment tool stand 60.

In this way, by making the configuration of the length of the second washing member 108 correspond to the shapes of the surfaces to be washed, it is possible to improve the washing efficiency of the treatment tool stand 60.

Third Modification Example

Figure 15:
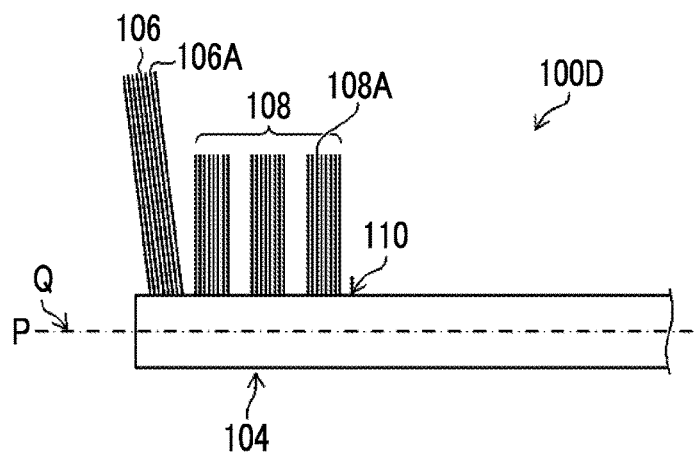
FIG. 15 is a schematic view illustrating the configuration of a stand washing tool as a third modification example.

FIG. 15 is a schematic view illustrating the configuration of a stand washing tool 100D as a third modification example. In FIG. 15, elements that are the same as or similar to those in FIG. 6 to FIG. 8 will be designated by the same reference signs, and the description thereof will be omitted. The first washing member 106 and the second washing member 108 in the third modification example are formed by using a plurality of brush hairs.

As illustrated in FIG. 15, the stand washing tool 100D as the third modification example is the same as that of the above-described embodiment in that the length of the first washing member 106 is longer than the length of the second washing member 108 and in that the second washing member 108 is erected in the direction perpendicular to the reference plane Q. However, the third modification example is different from the above-described embodiment in that the first washing member 106 is erected in a direction oblique to the raised direction of the second washing member 108.

Specifically, the first washing member 106 is erected such that the distance between the first washing member 106 and the second washing member 108 become larger toward the first end 106A (the distance from the washing member holding surface 110 increases). That is, the first washing member 106 is erected in a state where the first washing member 106 is inclined toward the distal end side of the head 104.

According to the stand washing tool 100D as the third modification example, similar to the above-described embodiment, the height position of the first end 106A of the first washing member 106 is higher than the height position of the second end 108A of the second washing member 108, and the first washing member 106 is inclined in a direction in which the first end 106A separates from the second washing member 108. Thus, in a case where the treatment tool stand 60 is washed, there is an advantage that the first washing member 106 is easily inserted into the gap 70 or 72.

In addition, in the third modification example, similar to the above-described embodiment, the height of the first end 106A of the first washing member 106 is made to be higher than the height of the second end 108A of the second washing member 108. However, the invention is not limited to this configuration. In a case where the length the first washing member 106 is made to be longer than the length of the second washing member 108, a height relationship between the height position of the first end 106A of the first washing member 106 and the height position of the second end 108A of the second washing member 108 does not matter. For example, the height position of the first end 106A of the first washing member 106 and the height position of the second end 108A of the second washing member 108 may be the same height position, or the height position of the second end 108A of the second washing member 108 may be higher than the height position of the first washing member 106.

In this way, according to the stand washing tool 100D in which at least the length of the first washing member 106 is made to be longer than the length of the second washing member 108, the distal end (first end 106A) of the first washing member 106 is easily inserted into the gap 70 or 72. Additionally, after the first washing member 106 is inserted into the gap 70 or 72, the first washing member 106 can be easily pushed into the deep part in conformity with the shape of the gap 70 or 72 due to the flexibility of the first washing member 106. Hence, it is possible to efficiently perform the operation of washing the treatment tool stand 60 in a short time without taking substantial time and effort.

Fourth Modification Example

Figure 16:
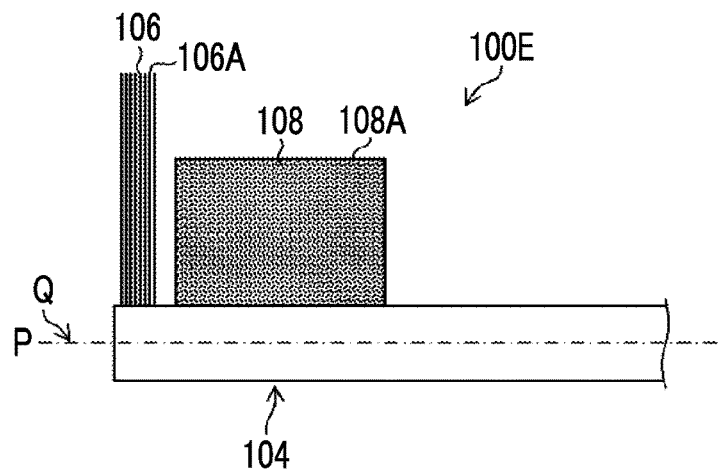
FIG. 16 is a schematic view illustrating the configuration of a stand washing tool as a fourth modification example.

FIG. 16 is a schematic view illustrating the configuration of a stand washing tool 100E as a fourth modification example. In FIG. 16, elements that are the same as or similar to those in FIG. 6 to FIG. 8 will be designated by the same reference signs, and the description thereof will be omitted.

As illustrated in FIG. 16, the stand washing tool 100E as the fourth modification example is same as the above-described embodiment in that the first washing member 106 is provided on the distal end side of the head 104, the second washing member 108 is provided on the handle side, and the height position of the first end 106A of the first washing member 106 is higher than the height position of the second end 108A of the second washing member 108. However, there is a difference that the first washing member 106 and the second washing member 108 are formed of different materials. Specifically, although the first washing member 106 is formed by using a plurality of brush hairs, the second washing member 108 is formed of a sponge member.

According to the stand washing tool 100E as the fourth modification example, the second washing member 108 is formed of the flexible sponge member. However, the second washing member 108 can be brought into close contact with and made to abut against the surfaces to be washed in conformity with the shapes thereof, and it is possible to improve the washing efficiency of the surface to be washed.

Fifth Modification Example

Figure 17:
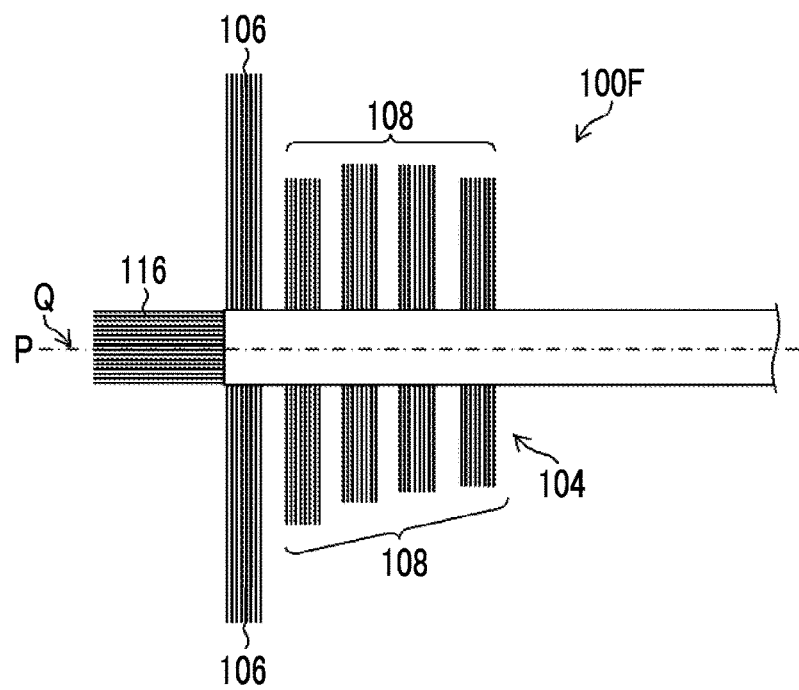
FIG. 17 is a schematic view illustrating the configuration of a stand washing tool as a fifth modification example.

FIG. 17 is a schematic view illustrating the configuration of a stand washing tool 100F as a fifth modification example. In FIG. 17, elements that are the same as or similar to those in FIG. 6 to FIG. 8 will be designated by the same reference signs, and the description thereof will be omitted. The first washing member 106, the second washing member 108, and a third washing member 116 in the fifth modification example are formed by using a plurality of brush hairs.

Although the stand washing tool 100F as the fifth modification example is the same as the above-described embodiment in that the first washing member 106 is erected on the distal end side of the head 104 and the second washing member 108 is erected on the handle side, the first washing member 106 and the second washing member 108 are respectively erected from both sides of the head 104 with respect to the reference plane Q.

Although the respective first washing members 106 and the respective second washing members 108 on both sides of the head 104 are formed in the direction perpendicular to the reference plane Q similar to the above-described embodiment, the length of the second washing member 108 becomes longer stepwise from the distal end side of the longitudinal axis P to a central part on one side (the upper side of the drawing) of the reference plane Q, and becomes shorter stepwise from the central part toward the proximal end side. Additionally, the length of the second washing member 108 becomes shorter stepwise toward the proximal end side of the longitudinal axis P on the other side (the lower side of the drawing) of the reference plane Q. Furthermore, the third washing member 116 extending toward the distal end side is provided on a distal end surface of the head 104. The third washing member 116 is made of a plurality of brush hairs, similar to the first washing member 106 or the second washing member 108.

According to the fifth modification example, a washing member to be used for washing can be selected and separately used in conformity with the shape of the treatment tool stand 60. For example, in a case where a convex surface like the treatment tool guide surface 62 or the gap 70 or 72 is washed, the washing can be performed using the washing members 106 and 108 on one side (the upper side of the drawing) of the reference plane Q, and in a case where washes a concave surface like the back surface 64 and the gap 70 or 72, the wash can be performed using the washing members 106 and 108 on the other side (the lower side of the drawing) of the reference plane Q. In a case where only the gap 70 or 72 is washed in addition to a series of washing operation, the washing can be performed using the third washing member 116 on the distal end side.

Although the first modification example to the fifth modification example have been described above, these modification examples can be appropriately combined together.

EXPLANATION OF REFERENCES

10: endoscope
12: insertion part
12a: distal end
12b: bending part
12c: flexible part
14: operating part
16: universal cord
18: angle knob
20: raising operating lever
21a: air/water supply button
21b: suction button
22: treatment tool inlet
30: distal end main body
32: cap
32A: opening window
34: flat surface
36: observation window
38: illumination window
39: air/water supply nozzle
40: stand accommodating slit
40a: opening
42: first side wall section
44: second side wall section
46: base wall section
48: stand storage wall section
60: treatment tool stand
60A: stand main body section
60B: rotating shaft holding section
62: treatment tool guide surface
64: back surface
70: gap
72: gap
80: raising lever
82: operation wire
90: base part end surface
92: rear end surface
100, 100A, 100B, 100C, 100D, 100E, 100F: stand washing tool
102: handle

104: head
106: first washing member
106A: first end
108: second washing member
108A: second end
110: washing member holding surface
112: first washing member holding surface
114: second washing member holding surface
116: third washing member

What is claimed is:

1. A method for washing a treatment tool stand of an endoscope, using a stand washing tool having
 a handle having a distal end, a proximal end, and a longitudinal axis,
 a head provided on a distal end side of the handle,
 a first washing member erected in a direction intersecting a reference plane including the longitudinal axis on the head, and
 a second washing member erected in a direction intersecting the reference plane on the head closer to the handle than the first washing member and provided so as to be parallel to or coincide with the first washing member in a case where the second washing member is projected on a plane perpendicular to the longitudinal axis,
 wherein the first washing member has a first end opposite to one end on the head side,
 wherein the second washing member has a second end opposite to one end on the head side,
 wherein a height position of the first end in a direction orthogonal to the reference plane from the reference plane is a first height position,
 wherein a height position of the second end in the direction orthogonal to the reference plane from the reference plane is a second height position lower than the first height position, the washing method comprising:
 a first washing member inserting step of inserting the first washing member into a gap between a stand storage wall section of the endoscope and the treatment tool stand;
 a second washing member abutting step of making the second washing member abut against a treatment tool guide surface of the treatment tool stand; and
 a stand washing tool moving step of moving the stand washing tool along the treatment tool guide surface in a state where the first washing member is inserted into the gap and the second washing member is made to abut against the treatment tool guide surface.

2. A method for washing a treatment tool stand of an endoscope, using a stand washing tool having
 a handle having a distal end, a proximal end, and a longitudinal axis,
 a head provided on a distal end side of the handle,
 a first washing member erected in a direction intersecting a reference plane including the longitudinal axis on the head, and
 a second washing member erected in a direction intersecting the reference plane on the head closer to the handle than the first washing member and provided so as to be parallel to or coincide with the first washing member in a case where the second washing member is projected on a plane perpendicular to the longitudinal axis,
 wherein the first washing member has a first end opposite to one end on the head side,
 wherein the second washing member has a second end opposite to one end on the head side,
 wherein a height position of the first end in a direction orthogonal to the reference plane from the reference plane is a first height position,
 wherein a height position of the second end in the direction orthogonal to the reference plane from the reference plane is a second height position lower than the first height position, the washing method comprising:
 a first washing member inserting step of inserting the first washing member into a gap between a stand storage wall section of the endoscope and the treatment tool stand;
 a second washing member abutting step of making the second washing member abut against a back surface opposite to a treatment tool guide surface of the treatment tool stand; and
 a stand washing tool moving step of moving the stand washing tool along the back surface in a state where the first washing member is inserted into the gap and the second washing member is made to abut against the back surface.

3. The method for washing a treatment tool stand according to claim 1,
 wherein, in the first washing member inserting step, the first washing member is inserted into the gap after the treatment tool stand is tilted.

4. The method for washing a treatment tool stand according to claim 2,
 wherein, in the first washing member inserting step, the first washing member is inserted into gap after the treatment tool stand is raised.

5. A method for washing a treatment tool stand of an endoscope, using a stand washing tool having
 a handle having a distal end, a proximal end, and a longitudinal axis,
 a head provided on a distal end side of the handle,
 a first washing member that is erected in a first direction intersecting a reference plane including the longitudinal axis on the head and has a first length in the first direction, and
 a second washing member that is erected in a second direction intersecting the reference plane on the head closer to the handle than the first washing member, is provided so as to be parallel to or coincide with the first washing member in a case where the second washing member is projected on a plane perpendicular to the longitudinal axis, and has a second length shorter than the first length in the second direction, the washing method comprising:
 a first washing member inserting step of inserting the first washing member into a gap between a stand storage wall section of the endoscope and the treatment tool stand;
 a second washing member abutting step of making the second washing member abut against a treatment tool guide surface of the treatment tool stand; and
 a stand washing tool moving step of moving the stand washing tool along the treatment tool guide surface in a state where the first washing member is inserted into the gap and the second washing member is made to abut against the treatment tool guide surface.

6. A method for washing a treatment tool stand of an endoscope, using a stand washing tool having
 a handle having a distal end, a proximal end, and a longitudinal axis, a head provided on a distal end side of the handle, a first washing member that is erected in a first direction intersecting a reference plane including the longitudinal axis on the head and has a first length in the first direction, and a second washing member that is erected in a second direction intersecting the reference plane on the head closer to the handle than the first washing member, is provided so as to be parallel to or coincide with the first washing member in a case where the second washing member is projected on a plane perpendicular to the longitudinal axis, and has a second length shorter than the first length in the second direction, the washing method comprising:

a first washing member inserting step of inserting the first washing member into a gap between a stand storage wall section of the endoscope and the treatment tool stand;

a second washing member abutting step of making the second washing member abut against a back surface opposite to a treatment tool guide surface of the treatment tool stand; and a stand washing tool moving step of moving the stand washing tool along the back surface in a state where the first washing member is inserted into the gap and the second washing member is made to abut against the back surface.

7. The method for washing a treatment tool stand according to claim 5, wherein, in the first washing member inserting step, the first washing member is inserted into the gap after the treatment tool stand is tilted.

8. The method for washing a treatment tool stand according to claim 6, wherein, in the first washing member inserting step, the first washing member is inserted into gap after the treatment tool stand is raised.

9. The method for washing a treatment tool stand according to claim 1, wherein the head has a washing member holding surface that holds the first washing member and the second washing member, and wherein $L1>L2$ is satisfied in a case where a length from the washing member holding surface of the first washing member to the first end is defined as $L1$ and a length from the washing member holding surface of the second washing member to the second end is defined as $L2$.

10. The method for washing a treatment tool stand according to claim 2, wherein the head has a washing member holding surface that holds the first washing member and the second washing member, and wherein $L1>L2$ is satisfied in a case where a length from the washing member holding surface of the first washing member to the first end is defined as $L1$ and a length from the washing member holding surface of the second washing member to the second end is defined as $L2$.

11. The method for washing a treatment tool stand according to claim 1, wherein the head has a first washing member holding surface that holds the first washing member and a second washing member holding surface that holds the second washing member, and wherein $L3+L4>L5$ is satisfied in a case where a height position of the first washing member holding surface in a direction orthogonal to the reference plane from the reference plane is a third height position, a height position of the second washing member holding surface in the direction orthogonal to the reference plane from the reference plane is a fourth height position lower than the third height position, a difference between the third height position and the fourth height position is defined as $L3$, a length from the first washing member holding surface of the first washing member to the first end is defined as $L4$, and a length from the second washing member holding surface of the second washing member to the second end is defined as $L5$.

12. The method for washing a treatment tool stand according to claim 2, wherein the head has a first washing member holding surface that holds the first washing member and a second washing member holding surface that holds the second washing member, and wherein $L3+L4>L5$ is satisfied in a case where a height position of the first washing member holding surface in a direction orthogonal to the reference plane from the reference plane is a third height position, a height position of the second washing member holding surface in the direction orthogonal to the reference plane from the reference plane is a fourth height position lower than the third height position, a difference between the third height position and the fourth height position is defined as $L3$, a length from the first washing member holding surface of the first washing member to the first end is defined as $L4$, and a length from the second washing member holding surface of the second washing member to the second end is defined as $L5$.

13. The method for washing a treatment tool stand according to claim 1, wherein the stand storage wall section has a first side wall section and a second side wall section that face each other with the treatment tool stand interposed therebetween, and a base wall section provided between a first side wall section and the second side wall section, and wherein the gap is a gap between the base wall section and the treatment tool stand.

14. The method for washing a treatment tool stand according to claim 2, wherein the stand storage wall section has a first side wall section and a second side wall section that face each other with the treatment tool stand interposed therebetween, and a base wall section provided between a first side wall section and the second side wall section, and wherein the gap is a gap between the base wall section and the treatment tool stand.

15. The method for washing a treatment tool stand according to claim 5, wherein the stand storage wall section has a first side wall section and a second side wall section that face each other with the treatment tool stand interposed therebetween, and a base wall section provided between a first side wall section and the second side wall section, and wherein the gap is a gap between the base wall section and the treatment tool stand.

16. The method for washing a treatment tool stand according to claim 6, wherein the stand storage wall section has a first side wall section and a second side wall section that face each other with the treatment tool stand interposed therebetween, and a base wall section provided between a first side wall section and the second side wall section, and wherein the gap is a gap between the base wall section and the treatment tool stand.

17. The method for washing a treatment tool stand according to claim 1,
wherein the first washing member is harder than the second washing member.

18. The method for washing a treatment tool stand according to claim 17,
wherein the first washing member is formed of a first material, and the second washing member is formed of a second material softer than the first material.

19. The method for washing a treatment tool stand according to claim 1,
wherein the first washing member and the second washing member have a plurality of brush hairs.

20. The method for washing a treatment tool stand according to claim 19,
wherein the brush hairs of the first washing member are thicker than the brush hairs of the second washing member.

* * * * *